United States Patent [19]

Hagen et al.

[11] Patent Number: 4,699,983
[45] Date of Patent: Oct. 13, 1987

[54] 2-AMINO-4-TRICHLOROMETHYLPYRI-DINE AND ITS PREPARATION

[75] Inventors: Helmut Hagen, Frankenthal; Hans Ziegler, Mutterstadt; Rolf-Dieter Kohler, Edingen-Neckarhausen; Ernst-Heinrich Pommer, Limburgerhof; Jürgen Dressel, Neuhofen, all of Fed. Rep. of Germany

[73] Assignee: BASF Aktiengesellschaft, Ludwigshafen, Fed. Rep. of Germany

[21] Appl. No.: 838,780

[22] Filed: Mar. 12, 1986

[30] Foreign Application Priority Data

Mar. 19, 1985 [DE] Fed. Rep. of Germany ....... 3509860

[51] Int. Cl.$^4$ .................... A01N 43/40; C07D 211/72
[52] U.S. Cl. ........................................ 546/311; 71/94; 546/272
[58] Field of Search ............................ 71/94; 546/311

[56] References Cited

U.S. PATENT DOCUMENTS 3,135,594  6/1964  Goring ................................ 546/345
3,682,936  8/1972  Tarba ................................. 546/311

Primary Examiner—Henry R. Jiles
Assistant Examiner—Robert C. Whittenbaugh
Attorney, Agent, or Firm—Keil & Weinkauf

[57] ABSTRACT

2-Amino-4-trichloromethylpyridine of the formula I

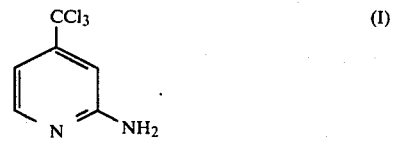

The compound is an effective nitrification inhibitor.

2 Claims, No Drawings

2-AMINO-4-TRICHLOROMETHYLPYRIDINE AND ITS PREPARATION

2-Chloro-6-trichloromethylpyridine is known to be a nitrification inhibitor; the common name of the active ingredient is nitrapyrin. Its preparation and action are described in, for example, U.S. Pat. No. 3,135,594.

The usefulness of this compound is restricted by its physical and chemical properties: because of the low vapor pressure, it is readily volatile, which makes it more difficult to use it as a nitrification inhibitor.

Aminohalopyridines are also known substances. Although they have been said to exhibit fungicidal, bactericidal and insecticidal actions, none of the substances of this group, which is described in, for example, U.S. Pat. No. 3,799,935, has become important in practice.

We have found that 2-amino-trichloromethylpyridine of the formula I

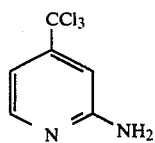

is very effective and, because of its physical properties and its high stability, has a wider range of uses and is more reliable in use.

2-Amino-4-trichloromethylpyridine can be obtained from 2-amino-4-picoline after appropriate protection of the amino group. The amino group can be protected by, for example, reaction with phthalic anhydride. Halogenation of the 4-methyl-2-phthalimidopyridine with chlorine to give 2-phthalimido-4-trichloromethylpyridine can be carried out in the reaction mixture, without isolation of this compound; the protective group is then eliminated by hydrolysis, ethanolamine having proven useful for this reaction.

To introduce the protective group, it is advantageous to use a solvent. Examples of suitable solvents are aromatics, such as benzene, toluene or xylene, aliphatic hydrocarbons, substituted aromatics, such as nitrobenzene or dichlorobenzene, and other halohydrocarbons, such as tetrachloroethane. The water formed is advantageously removed by azeotropic distillation. The reaction takes place at from 50° to 250° C., preferably from 100° to 180° C. If halogenation is to be carried out without isolating the intermediate, a solvent suitable for the halogenation is advantageously employed from the outset.

Chlorobenzene and dichlorobenzene are preferred, but, for example, nitrobenzene may also be used. A free radical former, such as azobisisobutyronitrile, is advantageously added, in an amount of from 0.1 to 10%, preferably from 0.5 to 1%, based on the compound being chlorinated. The reaction may also be accelerated with aid of a UV light source, in the usual manner. Chlorination is carried out at from 50° to 250° C., preferably from 120° to 160° C.

The hydrolysis is advantageously effected by the method described in German Laid-Open Application DOS No. 3,319,650.

For the hydrolysis, it is advisable to use as the solvent an excess of ethanolamine, water, an alcohol, such as ethanol, propanol or methylglycol, a ketone such as acetone, a chlorohydrocarbon, such as chloroform or an ether such as diethyl ether. An excess of ethanolamine, ethanol or propanol is preferred. The preferred temperature range for the hydrolysis is from −10° to 30° C.

EXAMPLE 108.1 g of 2-amino-4-picoline in 1 kg of 1,2-dichlorobenzene were refluxed with 148 g of phthalic anhydride for 2 hours at 170° C. under a condenser kept at above 100° C., and the water formed was distilled off. The mixture was cooled to 140° C., and 1 g of azobisisobutyronitrile was added. At 140° C., 400 g of chlorine were passed in, after which the mixture was cooled, some of the solvent was removed under reduced pressure, and petroleum ether was added to the residue. The precipitate was separated off, washed with petroleum ether and dried. 320 g (94% of theory) of 2-phthalimido-4-trichloromethylpyridine of melting point 143° C. were obtained.

105 g of the intermediate were introduced into 600 g of ethanolamine at from 20° to 30° C. After 30 minutes, the mixture was poured into 2 l of ice water, and the precipitate was separated off, washed with water and dried. 122 g (96%) of 2-amino-4-trichloromethylpyridine of melting point 114° C. were obtained.

EXAMPLE OF USE 220 mg of ammonium sulfate were added to 200 g of an unsterilized loamy sand soil which had been taken from open ground and whose moisture content had been adjusted to 50% of the maximum water capacity, and the ammonium sulfate was mixed thoroughly with the soil. Thereafter, the active ingredients, dissolved in 0.2 ml of acetone, were added in each case in amounts of 2, 1, 0.5 and 0.25 ppm, based on moist sand soil. After careful mixing and evaporation of the acetone, the soil samples, as well as the controls without added active ingredient, were incubated for 28 days at 21° C. in 1 liter glass vessels covered with aluminum foil to prevent water losses (after this period, a soil sample in which soil conditions are normal generally no longer contains any detectable amounts of ammonium nitrogen).

2.5 g of each of the soil samples were then introduced into 100 ml conical flasks, and 22.5 ml of a 0.1-N potassium sulfate solution were added. After shaking for 30 minutes, the mixtures were filtered, and 2.5 ml of each of the soil extracts were mixed with 1625 ml of distilled water. To detect any ammonium ions still present in the soil extract, 1.25 ml of Nessler's reagent were then added and the mixture shaken thoroughly. The color changes were then measured photometrically at a wavelength of 420 nm. By reference to standard curves determined by measuring solutions containing known amounts of ammonium sulfate, the amounts of ammonium sulfate still present in the soil samples were determined. The percentage inhibition of nitrification in the treated soil samples was calculated by comparison with the untreated soil samples (only ammonium sulfate added) using the following formula:

$$\% \text{ inhibition of nitrification} = \frac{a - b}{a} \cdot 100$$

a = nitrification rate of ammonium sulfate (taken as 100% or 1.0)
b = nitrification rate of ammonium sulfate + nitrification inhibitor

| Amount of active ingredient added ... ppm | ... % inhibition of nitrification 4 weeks after the addition of 2-amino-4-trichloromethylpyridine to the soil |
| --- | --- |
| 2 | 100 |
| 1 | 97 |
| 0.5 | 94 |
| 0.25 | 48 |

We claim:

1. 2-Amino-4-trichloromethylpyridine of the formula I

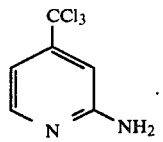

2. A process for the preparation of 2-amino-4-trichloromethylpyridine of the formula I, wherein 2-amino-4-picoline is reacted with phthalic anhydride to give 4-methyl-2-phthalimidopyridine, the latter is chlorinated and the product is hydrolyzed.

* * * * *